(12) United States Patent
Patterson et al.

(10) Patent No.: US 9,884,165 B2
(45) Date of Patent: Feb. 6, 2018

(54) MULTI-LUMEN CATHETER INCLUDING AN ELLIPTICAL PROFILE

(75) Inventors: Ryan C. Patterson, Farmington, UT (US); John W. Hall, North Salt Lake, UT (US); Jeremy C. Horton, Salt Lake City, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 1388 days.

(21) Appl. No.: 13/370,128

(22) Filed: Feb. 9, 2012

(65) Prior Publication Data

US 2012/0209221 A1    Aug. 16, 2012

Related U.S. Application Data

(60) Provisional application No. 61/441,566, filed on Feb. 10, 2011.

(51) Int. Cl.
*A61M 25/00* (2006.01)

(52) U.S. Cl.
CPC .... *A61M 25/0032* (2013.01); *A61M 25/0021* (2013.01); *A61M 25/0023* (2013.01);
(Continued)

(58) Field of Classification Search
CPC .............. A61M 25/00; A61M 25/0021; A61M 25/0023; A61M 25/0029; A61M 25/003; A61M 25/0032; A61M 25/0043; A61M 25/0052; A61M 25/0071; A61M 25/0074; A61M 2025/00; A61M 2025/0021; A61M 2025/0023; A61M 2025/003; A61M 2025/0035; A61M 2025/0073; A61M 2025/0025; A61M 2025/0034; A61M 2025/0037
(Continued)

(56) References Cited

U.S. PATENT DOCUMENTS

| 3,672,372 A | 6/1972 | Heimlich |
|---|---|---|
| 4,257,422 A | 3/1981 | Duncan |

(Continued)

FOREIGN PATENT DOCUMENTS

| EP | 0711574 A1 | 5/1996 |
|---|---|---|
| EP | 1694382 B1 | 8/2010 |

(Continued)

OTHER PUBLICATIONS

PCT/US2012/024514 filed Feb. 9, 2012 International Search Report and Written Opinion dated Sep. 11, 2012.
(Continued)

*Primary Examiner* — Rebecca E Eisenberg
(74) *Attorney, Agent, or Firm* — Rutan & Tucker, LLP (57) ABSTRACT

A multi-lumen catheter including an elliptical cross-sectional profile configuration that enhances fluid flow rate while minimizing the average diameter of the catheter body is disclosed. In one embodiment the catheter comprises an elongate catheter tube defining a plurality of lumens. At least a portion of the longitudinal length of the catheter tube defines an elliptical cross section, in turn defined by a major axis and a minor axis. A ratio of the major axis to the minor axis of the elliptical catheter tube cross section is between about 1.3 and about 1.4 in one embodiment. The catheter body can define two, three, or more lumens, in one embodiment.

28 Claims, 11 Drawing Sheets

(52) U.S. Cl.
CPC . *A61M 25/0043* (2013.01); *A61M 2025/0025* (2013.01); *A61M 2025/0034* (2013.01); *A61M 2025/0035* (2013.01); *A61M 2025/0037* (2013.01)

(58) Field of Classification Search
USPC .......................................... 604/264, 523, 284
See application file for complete search history.

(56) References Cited

U.S. PATENT DOCUMENTS

| | | | |
|---|---|---|---|
| 4,405,313 A | 9/1983 | Sisley et al. | |
| 4,619,643 A | 10/1986 | Bai | |
| 4,639,252 A | 1/1987 | Kelly et al. | |
| 4,681,570 A | 7/1987 | Dalton | |
| 5,057,073 A | 10/1991 | Martin | |
| 5,221,256 A | 6/1993 | Mahurkar | |
| 5,303,704 A | 4/1994 | Molacek et al. | |
| 5,322,519 A | 6/1994 | Ash | |
| 5,451,206 A | 9/1995 | Young | |
| 5,486,159 A * | 1/1996 | Mahurkar | 604/6.16 |
| 5,556,390 A * | 9/1996 | Hicks | 604/523 |
| 5,566,680 A | 10/1996 | Urion et al. | |
| 5,762,629 A | 6/1998 | Kambin | |
| 5,795,326 A * | 8/1998 | Siman | 604/43 |
| 5,807,311 A | 9/1998 | Palestrant | |
| 5,807,349 A | 9/1998 | Person et al. | |
| 5,858,009 A | 1/1999 | Jonkman | |
| 6,004,302 A | 12/1999 | Brierley | |
| 6,146,354 A | 11/2000 | Beil | |
| 6,146,371 A | 11/2000 | DeWindt et al. | |
| 6,270,477 B1 | 8/2001 | Bagaoisan | |
| 6,293,927 B1 | 9/2001 | McGuckin, Jr. | |
| 6,461,321 B1 | 10/2002 | Quinn | |
| 6,544,218 B1 | 4/2003 | Choi | |
| 6,595,966 B2 | 7/2003 | Davey et al. | |
| 6,695,832 B2 | 2/2004 | Schon et al. | |
| 6,719,749 B1 | 4/2004 | Schweikert et al. | |
| 6,749,580 B2 | 6/2004 | Work et al. | |
| 6,758,836 B2 | 7/2004 | Zawacki | |
| 6,814,718 B2 | 11/2004 | McGuckin, Jr. et al. | |
| 6,881,211 B2 | 4/2005 | Schweikert et al. | |
| 6,911,014 B2 | 6/2005 | Wentling et al. | |
| 7,077,829 B2 | 7/2006 | McGuckin, Jr. et al. | |
| 7,108,674 B2 | 9/2006 | Quinn | |
| 7,141,035 B2 | 11/2006 | Haggstrom | |
| 7,276,055 B2 | 10/2007 | DeWindt et al. | |
| 7,322,953 B2 | 1/2008 | Redinger | |
| 7,500,949 B2 | 3/2009 | Gottlieb et al. | |
| 7,556,612 B2 | 7/2009 | Voorhees | |
| RE40,913 E | 9/2009 | Schweikert | |
| 7,695,450 B1 | 4/2010 | Twardowski et al. | |
| 7,740,780 B2 | 6/2010 | Hamboly | |
| 7,776,005 B2 | 8/2010 | Haggstrom et al. | |
| 7,918,817 B2 | 4/2011 | Schon et al. | |
| 7,967,788 B2 | 6/2011 | Chandrasekar et al. | |
| 7,981,093 B2 | 7/2011 | Schon et al. | |
| 8,021,321 B2 | 9/2011 | Zawacki | |
| 8,092,415 B2 | 1/2012 | Moehle | |
| 8,137,309 B2 | 3/2012 | Nishtala et al. | |
| 8,167,867 B2 | 5/2012 | Briscoe et al. | |
| 2003/0097099 A1* | 5/2003 | Quinn | 604/270 |
| 2004/0034333 A1 | 2/2004 | Seese et al. | |
| 2004/0210187 A1* | 10/2004 | Zawacki | 604/43 |
| 2005/0015048 A1 | 1/2005 | Chiu et al. | |
| 2005/0096585 A1 | 5/2005 | Schon et al. | |
| 2006/0020256 A1* | 1/2006 | Bell et al. | 604/523 |
| 2006/0135916 A1 | 6/2006 | Tucker | |
| 2006/0184097 A1 | 8/2006 | Quinn | |
| 2007/0005003 A1 | 1/2007 | Patterson et al. | |
| 2007/0083161 A1 | 4/2007 | Briscoe et al. | |
| 2007/0106211 A1 | 5/2007 | Provost-Tine et al. | |
| 2008/0033372 A1 | 2/2008 | Briscoe et al. | |
| 2008/0097350 A1* | 4/2008 | Bell et al. | 604/266 |
| 2008/0114335 A1 | 5/2008 | Flickinger et al. | |
| 2008/0249420 A1 | 10/2008 | Crossman | |
| 2009/0024108 A1 | 1/2009 | Lee-Sepsick et al. | |
| 2009/0054874 A1 | 2/2009 | Barron et al. | |
| 2009/0088699 A1* | 4/2009 | King et al. | 604/175 |
| 2009/0125120 A1 | 5/2009 | McWeeney | |
| 2009/0171318 A1 | 7/2009 | Drewes, Jr. | |
| 2009/0192435 A1 | 7/2009 | Gregersen | |
| 2009/0209940 A1 | 8/2009 | Nimkar et al. | |
| 2009/0247868 A1 | 10/2009 | Chesnin | |
| 2010/0152707 A1 | 6/2010 | Morris et al. | |
| 2010/0168642 A1 | 7/2010 | Appling et al. | |
| 2010/0191165 A1 | 7/2010 | Appling et al. | |
| 2010/0298859 A1* | 11/2010 | Miller et al. | 606/192 |
| 2011/0004197 A1 | 1/2011 | Sansoucy | |
| 2011/0105984 A1* | 5/2011 | Patel et al. | 604/6.16 |
| 2011/0251564 A1 | 10/2011 | Chandrasekar et al. | |
| 2012/0041419 A1 | 2/2012 | Blanchard et al. | |
| 2012/0065579 A1 | 3/2012 | Cully et al. | |
| 2013/0261605 A1 | 10/2013 | Gregersen et al. | |

FOREIGN PATENT DOCUMENTS

| | | |
|---|---|---|
| EP | 2228091 A1 | 9/2010 |
| WO | 1996020752 A1 | 7/1996 |
| WO | 2001056630 A1 | 8/2001 |
| WO | 2005072806 A3 | 2/2006 |
| WO | 2007050296 A1 | 5/2007 |
| WO | 2006119422 A3 | 9/2007 |
| WO | 2007120505 A1 | 10/2007 |
| WO | 2009051969 A1 | 4/2009 |
| WO | 2011008896 A3 | 5/2011 |
| WO | 2012109462 A2 | 8/2012 |
| WO | 2013177549 A1 | 11/2013 |

OTHER PUBLICATIONS

PCT/US2013/042717 filed May 24, 2013 International Search Report and Written Opinion dated Nov. 5, 2013.
CN 201380036556.X filed Jan. 8, 2015 First Office Action dated Jul. 19, 2016.
U.S. Appl. No. 13/902,488, filed May 24, 2013 Final Office Action dated Sep. 20, 2016.
EP 13793874.2 filed Dec. 17, 2014 Extended European Search Report dated Apr. 5, 2016.
EP 13793874.2 filed Dec. 17, 2014 Partial European Search Report dated Jan. 8, 2016.
U.S. Appl. No. 13/902,488, filed May 24, 2013 Non-Final Office Action dated Mar. 1, 2016.

* cited by examiner

MULTI-LUMEN CATHETER INCLUDING AN ELLIPTICAL PROFILE

CROSS-REFERENCE TO RELATED APPLICATIONS

This application claims the benefit of U.S. Provisional Patent Application No. 61/441,566, filed Feb. 10, 2011, and titled "Multi-Lumen Catheter Including an Elliptical Profile," which is incorporated herein by reference in its entirety.

BRIEF SUMMARY

Briefly summarized, embodiments of the present invention are directed to a multi-lumen catheter including an elliptical cross-sectional profile configuration that enhances fluid flow rate while minimizing the average diameter of the catheter body. In one embodiment the catheter comprises an elongate catheter tube defining a plurality of lumens. At least a portion of the longitudinal length of the catheter tube defines an elliptical cross section, in turn defined by a major axis and a minor axis. A ratio of the major axis to the minor axis of the elliptical catheter tube cross section is between about 1.3 and about 1.4, in one embodiment. In another embodiment the ratio is about 1.33 in order to optimize lumen flow characteristics. The elliptical profile in one embodiment can also serve to enhance biocompatibility and kink resistance.

Though beneficially applicable to catheters of many configurations, it is appreciated that relatively thick-walled catheters, e.g., catheters including a relatively weak material such as silicone, can also benefit from the enhanced flow characteristics of the elliptic lumen profile disclosed herein. It is appreciated that the catheter body can define two, three, or more lumens, in one embodiment.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments described herein are generally directed to a multi-lumen catheter profile configuration that enhances fluid flow rate through the lumens thereof while minimizing the average diameter of the catheter body. In one embodiment, the catheter includes an elliptical profile with a predetermined aspect ratio to enhance flow performance, biocompatibility, and/or kink resistance. In one embodiment, the aspect ratio of is about 1.3. Though beneficially applicable to catheters of many configurations, it is appreciated that relatively thick-walled catheters, e.g., catheters including a relatively weak material such as silicone, can also benefit from the enhanced flow characteristics of the elliptic lumen profile disclosed herein. The catheter body can define two, three, or more lumens, in one embodiment.

Figures 1A, 1B:
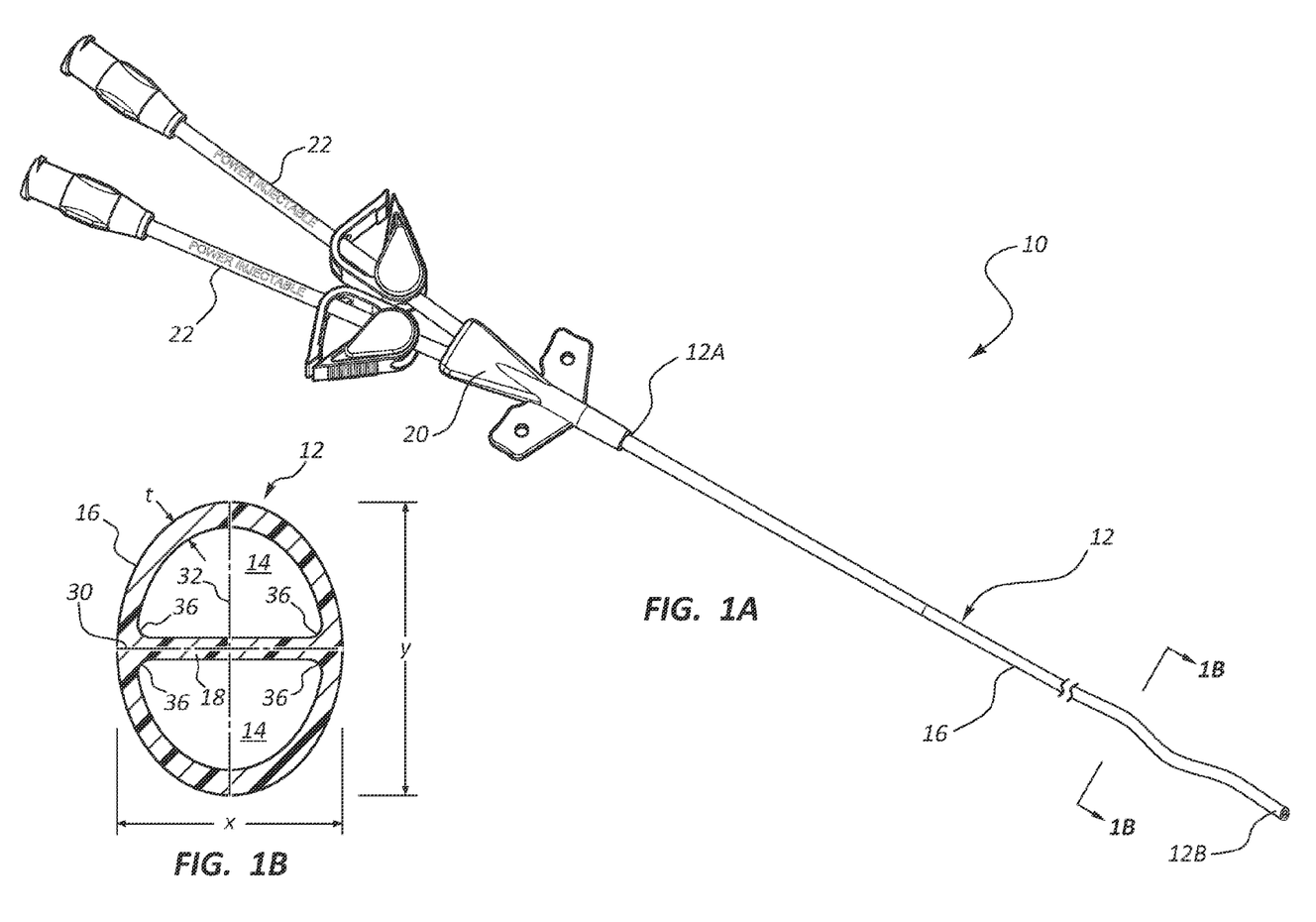
FIGS. 1A and 1B are perspective and cross sectional views, respectively, of a catheter assembly configured in accordance with one embodiment.

Reference is first made to FIG. 1, which depicts a catheter assembly, generally designated at 10, configured in accordance with one embodiment. As shown, the catheter assembly ("catheter") 10 includes an elongate catheter tube 12 formed by an outer wall 16 which, together with a septum 18 (FIG. 1B) defines two (or more) lumens 14 longitudinally extending between a proximal end 12A and a distal end 12B of the tube. A bifurcation 20 mates with the catheter tube 12 at the proximal end 12A thereof to provide fluid communication between the catheter tube and one or more extension legs 22.

FIG. 1B is a cross-sectional view of the catheter tube 12 of FIG. 1A, according to the present embodiment, wherein the catheter tube is aligned such that the width thereof extends along an x-axis and the height thereof extends along a y-axis, the x and y-axes being depicted in FIG. 1B and selected succeeding figures. As shown, the tube 12 cross-sectionally defines two lumens in a generally double-D configuration. Note that the corners 36 of each lumen 14 where the septum 18 joins with the outer wall 16 are rounded to provide more laminar flow through the lumen. The tube 12 further cross-sectionally defines an elliptical profile, further defined by a minor axis 30 parallel to the x-axis and a major axis 32 parallel to the y-axis, in the orientation shown in FIG. 1B. Both the minor and major axes 30, 32 are measured from the perimeter, or outer diameter ("OD") of the catheter tube outer wall 16 in the present embodiment. Note that, though in the present embodiment the elliptical nature of the catheter tube profile extends substantially the entire length of the tube, in other embodiments the elliptical profile can be included on less than the entire catheter tube length.

In the illustrated embodiment, the ratio between the major and minor axes 30 and 32, or aspect ratio, falls within a range that provides each lumen 14 a lumen height greater than that of lumens found in a cross-sectionally round catheter tube. This relatively increases the area of each lumen over those of a round tube, which in turn lessens the hydraulic resistance of fluid flowing through the respective lumen as seen by the following proportionality:

$$\text{hydraulic resistance} \propto p^2/A^3, \quad (1)$$

where p is the lumen perimeter and A is the lumen area. In one embodiment, the aspect ratio of the major and minor axes 30 and 32 falls within a range from about 1.3 to about 1.4. In another embodiment, the aspect ratio is about 1.33. Generally, the elliptical cross sectional profile of the catheter tube 12, as shown here and in the succeeding elliptical profile configurations, enhances fluid flow characteristics, while maintaining a low average diameter for minimizing blood flow obstruction when the catheter is disposed within the vasculature of a patient. Note that in one embodiment the average diameter of the catheter is defined as the sum of catheter ODs at the major axis and the minor axis, divided by two.

Figure 2:
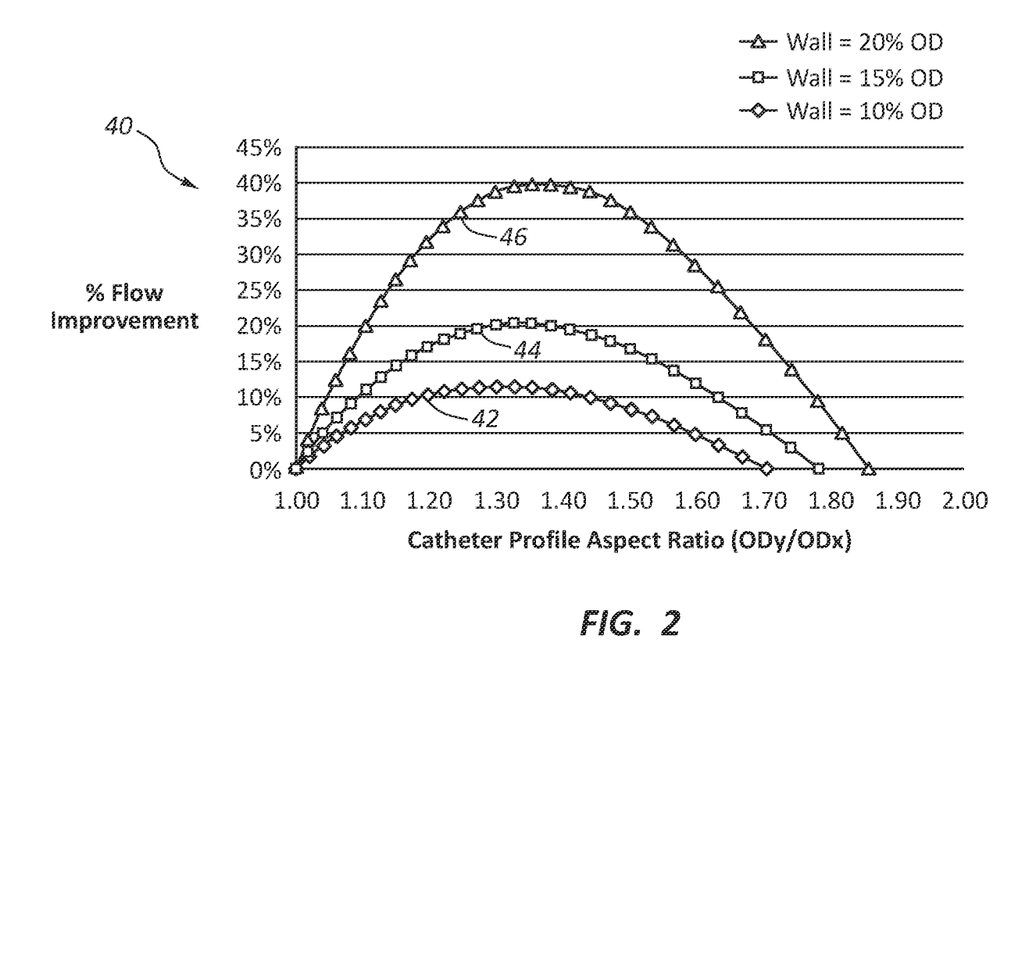
FIG. 2 is a graph demonstrating certain operating principles of catheter assemblies described herein in accordance with one embodiment.

The flow improvements realized by the elliptical lumen configurations shown in FIG. 1A and various other figures herein are depicted in a graph 40 of FIG. 2. In particular, graph 40 shows a bottom curve 42, middle curve 44, and an upper curve 46 that represent flow improvements as the aspect ratio of the catheter tube is increased in its elliptic nature from a round profile for each of three catheter tubes having an outer wall thickness t (indicated in FIG. 1B) equaling 10%, 15%, and 20% of the outer diameter of the catheter tube, respectively. As shown, the flow improvement for each curve 42, 44, and 46 is maximized at an aspect ratio between about 1.3 and about 1.4.

As shown by the curve 46, flow improvement is maximized for an elliptically-profiled catheter tube when the wall thickness t (see, e.g., FIG. 1B) of the catheter tube equals about 20% of the average outer catheter tube diameter. This relationship thus favors relatively thicker catheter tube walls, such as may be the case when relatively weak materials such as silicone, as employed to form the catheter tube. Note, however, that the catheter tube may be formed of any acceptable material, including polyurethanes and other thermoplastics, thermosets, etc.

Because of the elliptical nature of the catheter tube 12 as shown here, the width of the septum 18 in extending between opposite sides of the outer wall 16 to help define the two lumens 14 is shorter relative to the septum width in a correspondingly sized catheter tube with a circular cross-sectional profile. This in turn enables the septum to be stiffer in the elliptical catheter tube, which in turn helps prevent undesired septum deflection when pressure differentials exist between the lumens, such as in dialysis applications for instance. Optionally, this also enables the septum to be made thinner without compromising the rate of septum deflection over a septum of a round catheter tube.

Note that in the present embodiment shown in FIG. 1A, the bifurcation 20 provides fluid paths to establish fluid communication between the cross-sectionally round extension legs 22 and the lumens of the elliptically-shaped catheter tube 12. As such, the fluid paths defined in the bifurcation 20 in one embodiment can transition in cross-sectional shape from substantially round proximate the extension legs 22 to substantially elliptical proximate the bifurcation connection point with the proximal end 12A of the catheter tube 12. This can in turn further enhance fluid flow for the catheter assembly. In one embodiment, elliptical core pins are employed during manufacture of the bifurcation and catheter tube to provide properly shaped fluid paths within the bifurcation. The bifurcation in other embodiments can define other shaped fluid paths. Indeed, in one embodiment both the catheter tube and the extension legs can include elliptical cross-sectional shapes, and as such the bifurcation can define substantially elliptical cross-sectional fluid paths. These and other modifications are contemplated.

Figure 3:
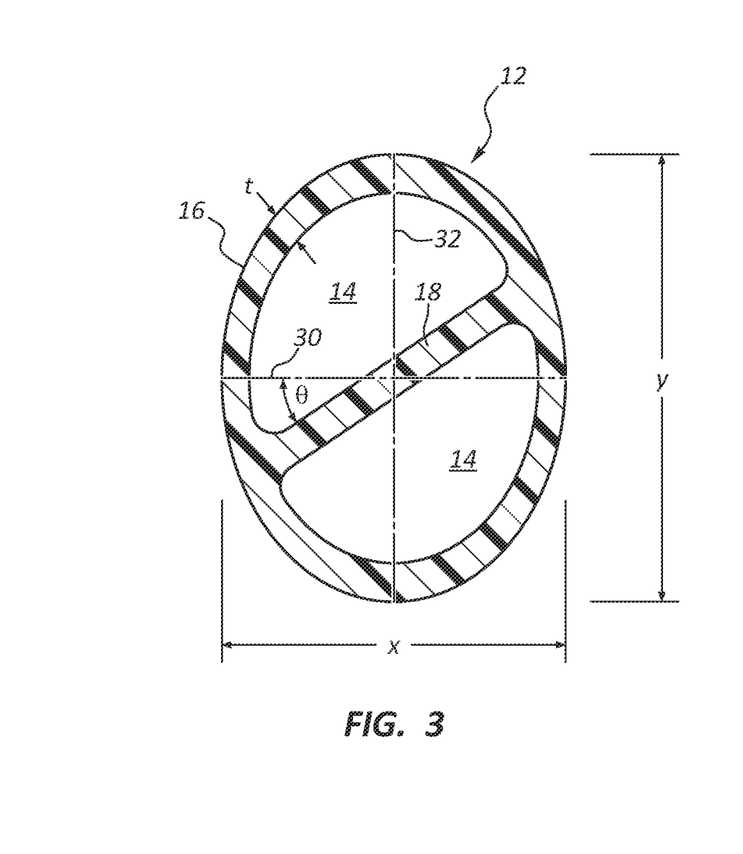
FIG. 3 is a cross sectional view of a catheter tube configured in accordance with one embodiment.

FIG. 3 shows a cross section of the catheter tube 12 according to another embodiment, wherein the elliptical profile is retained as defined by the minor and major axes 30, 32, but the septum 18 of the tube is slanted so as to define an angle θ with the minor axis 30. The slanted septum configuration illustrated in FIG. 3 provides in one embodiment relatively greater stability for the distal tip of the catheter during fluid infusion therethrough. This distal tip stability is at least partially due to the relatively larger product of the moment area of inertia I and the cross-sectional area A of the infusion lumen of the slanted septum configuration when compared with the product of I and A of a non-slanted septum configuration. The slanted septum configuration further balances the principal axis of I for the catheter tube, thus reducing the likelihood of the catheter tube to roll or bend in only one direction.

Figure 4:
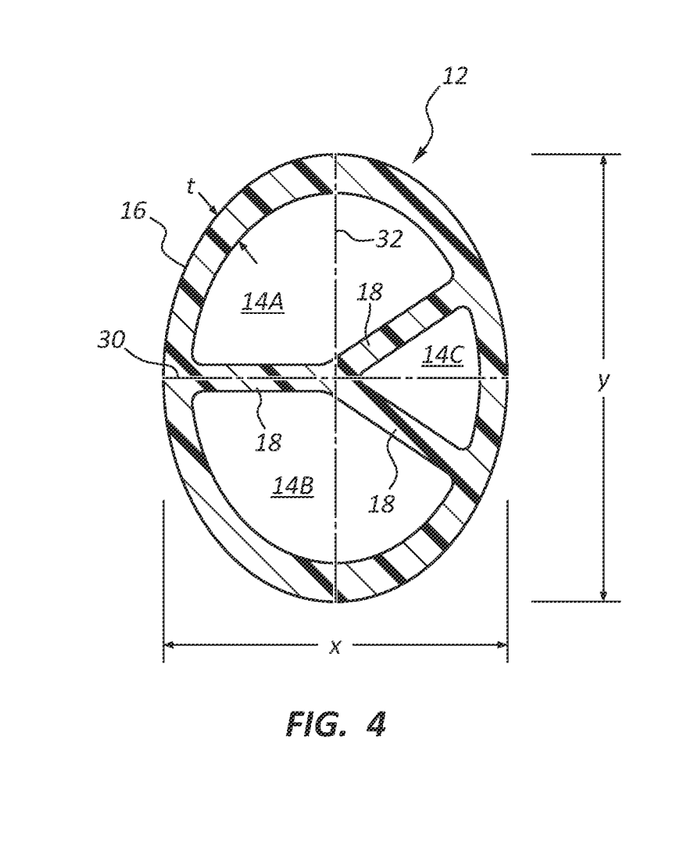
FIG. 4 is a cross sectional view of a catheter tube configured in accordance with one embodiment.

FIG. 4 shows a cross section of the catheter tube 12 according to another embodiment, wherein the elliptical profile is retained as defined by the minor and major axes 30, 32, but the tube defines three lumens 14A, 14B, and 14C in a triple lumen configuration. As shown, the septum 18 splits to border either side of the generally triangular third lumen 14C. As was the case with dual lumen catheter tube, the triple lumen configuration shown here improves flow rates for each of the lumens 14A, 14B, and 14C due to the elliptical catheter tube profile. It is noted that in one embodiment, one or more of the lumens 14A-14C can be configured for relatively high fluid flow rates therethrough, commonly referred to as power injection. Indeed, in the other embodiments herein described, one or more of the lumens of the catheter tube can be configured to withstand power injection.

Figure 5:
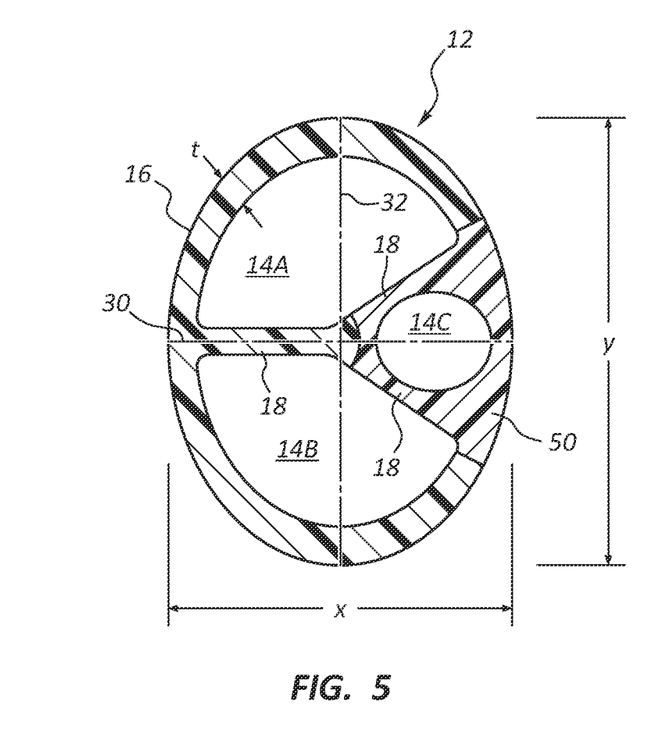
FIG. 5 is a cross sectional view of a catheter tube configured in accordance with one embodiment.

FIG. 5 shows a cross section of the catheter tube 12 according to another embodiment, wherein the elliptical profile is retained as defined by the minor and major axes 30, 32, and the tube defines three lumens 14A, 14B, and 14C in a triple lumen configuration, as in FIG. 4, wherein the septum 18 splits to border either side of the now circular third lumen 14C. Again, and as was the case with dual lumen catheter tube, the triple lumen configuration shown here improves flow rates for each of the lumens 14A, 14B, and 14C due to the elliptical catheter tube profile.

In contrast to the configuration of FIG. 4, the catheter tube 12 in FIG. 5 includes a portion 50 defining the portions of the outer wall 16 and the septum 18 that bound the third lumen 14C. The portion 50 extends longitudinally the length of the catheter tube and includes a relatively harder material than that of the material defining the rest of the septum 18 and outer 16. This relatively harder material reinforces the third lumen 14C to enable it to withstand the high fluid pressures typically associated with power injection.

Also, in one embodiment the material included in the portion 50 enables the portions of the outer wall 16 and septum 18 thinner than what would otherwise be possible, in turn enabling the other lumens 14A and 14B to be larger than they would otherwise be. In other embodiments, the material defining the portion 50 can also be stiffer and/or include greater tensile strength relative to the other portions of the outer wall and septum so as to provide the desired characteristics for the third lumen. In yet another embodiment, the portion 50 can extend to encompass the entirety of the septum 18.

Note that, as was the case with the elliptical dual lumen configurations above, the width of the septa 18 of triple and quad lumen configurations discussed here are shorter relative to the septa in correspondingly sized catheter tubes with a circular cross-sectional profiles. Again, this stiffens the septum, which in turn helps prevent undesired septum deflection when pressure differentials exist between the lumens.

In one embodiment, for example, the catheter portion 50 includes a material of hardness of about 100 Shore A, while the remaining portions of the catheter tube 12 include a material of hardness of about 85 Shore A. Thermoplastic polyurethanes including those sold under the names TECOTHANE® and CARBOTHANE® are non-limiting examples of materials that can be configured to meet the above or other desired hardness characteristics for the portion 50 and remaining portions of the catheter tube 12. The catheter tube 12 as shown in FIG. 5 and in the other figures discussed herein can be formed via co-extrusion, insert extrusion, and other suitable methods.

Note that a catheter assembly including a catheter tube as discussed above in connection with FIGS. 4 and 5 can be employed, for instance, for dialysis procedures wherein the third lumen is configured for power injection into the patient's vasculature. However, it should be appreciated that these and the other elliptical catheter tube configurations discussed herein can be employed in a variety of catheter applications, catheter types, and lumen number/configurations.

Figure 6:
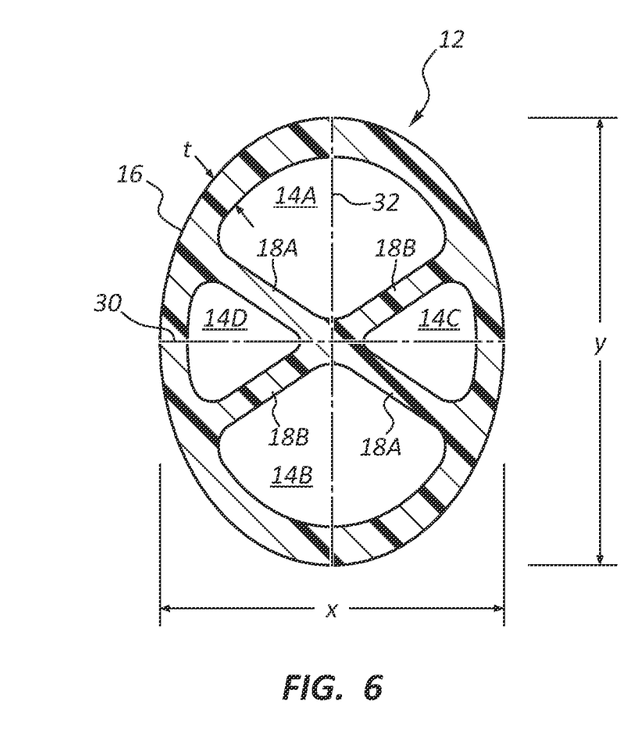
FIG. 6 is a cross sectional view of a catheter tube configured in accordance with one embodiment.

FIG. 6 shows a cross section of the catheter tube 12 according to another embodiment, wherein the elliptical profile is retained as defined by the minor and major axes 30, 32, but the tube now defines four lumens 14A, 14B, 14C, and 14D in a quad lumen configuration. As shown, two septa 18A and 18B intersect one another to define, together with the outer wall 16, the four lumens 14A-14D. As before one, two, or more of the lumens 14A-14D can be configured for power injection and flow therethrough is optimized due to the elliptical aspect ratio of the catheter tube 12.

Figure 7:
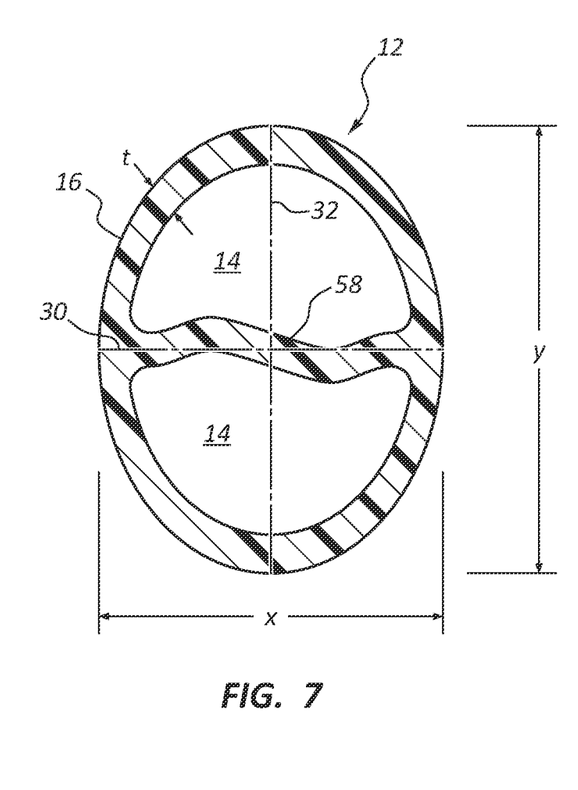
FIG. 7 is a cross sectional view of a catheter tube configured in accordance with one embodiment.
Figure 8A:
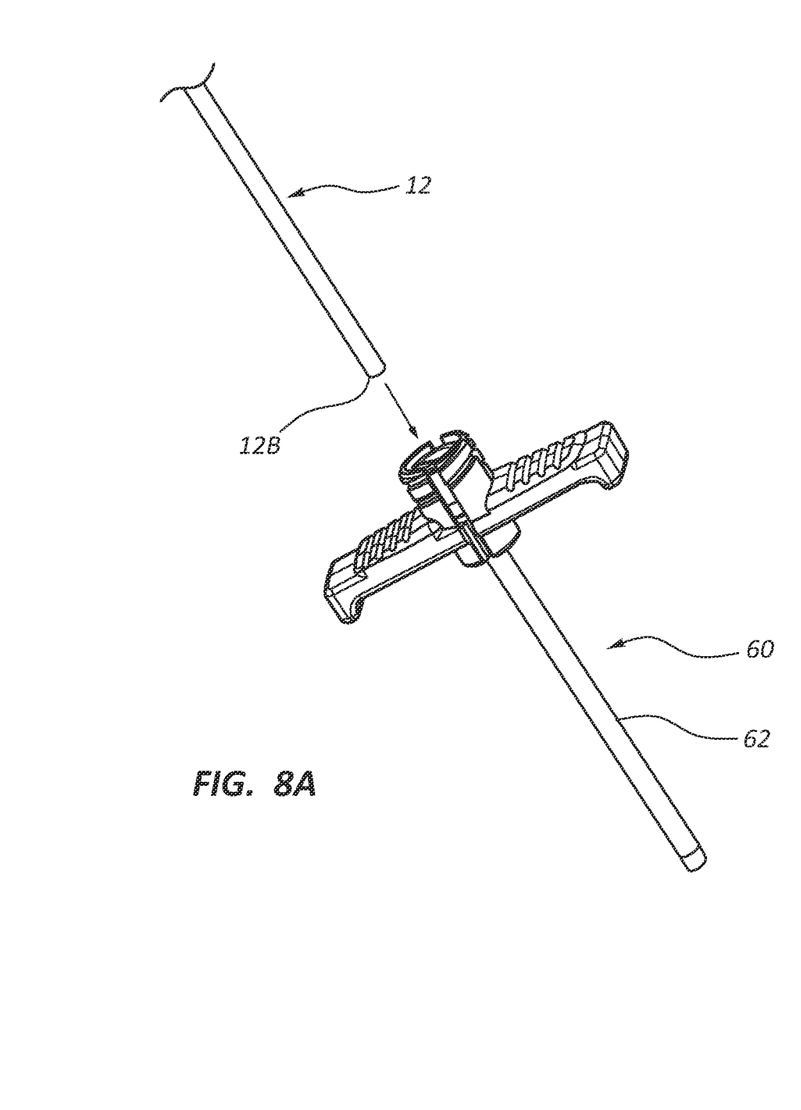
FIGS. 8A and 8B are perspective and cross sectional views, respectively, showing insertion and disposal of the catheter tube of FIG. 7 within an introducer, according to one embodiment.

FIG. 7 shows a cross section of the catheter tube 12 according to another embodiment, wherein the elliptical profile is retained as defined by the minor and major axes 30, 32. A septum 58 dividing the two lumens 14 is also shown. The septum 58 is initially slackened when the catheter tube 12 is in a rest state as shown in FIG. 7. This enables the elliptical catheter tube 12 to be fed through a round catheter introducer, such as the introducer 60 shown in FIG. 8A. In particular, FIG. 8A shows that catheter tube 12 of FIG. 7 being introduced into the proximal end of the introducer 60. The introducer 60 includes a round body 62, a portion of which is initially disposed within a vessel of the patient.

Figure 8B:
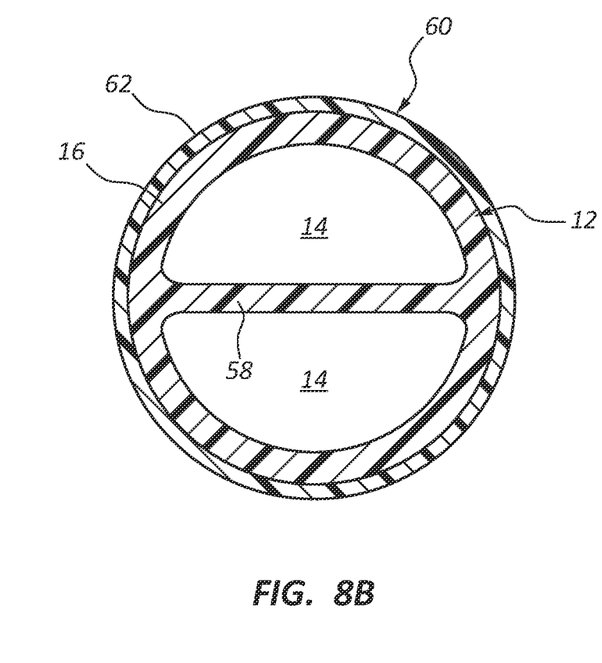

Introduction of the elliptical catheter tube 12 into the round introducer body 62 forces the tube outer wall 16 to deform into the round shape of the introducer body. Because of the initially slackened state of the septum 58, the catheter tube 12 is able to be deformed from the elliptical to the circular shape when it passes into the round introducer body 62. This causes the initially slackened septum 58 to be stretched taut as the outer body 16 of the catheter tube 12 is forced into the circular shape, as shown in FIG. 8B, which shows the catheter tube 12 disposed within the introducer body 62. This enables the catheter tube 12 to be inserted into the patient's vessel, after which the introducer 60 can be removed from the vessel and the catheter tube resiliently returns to its elliptical aspect profile (FIG. 7).

In one embodiment, a proximal portion of the introducer and/or introducer body can include a transition region that gradually changes from an elliptical profile to a round profile so as to ease insertion of the initially elliptical catheter tube into the introducer. In another embodiment, an elliptical introducer may be used to place the elliptical catheter tube into the patient's vasculature. Note that the slackened shape of the septum can vary from the wavy configuration shown in FIG. 7, including a bowed or arced shaped, for instance.

Figure 9A:
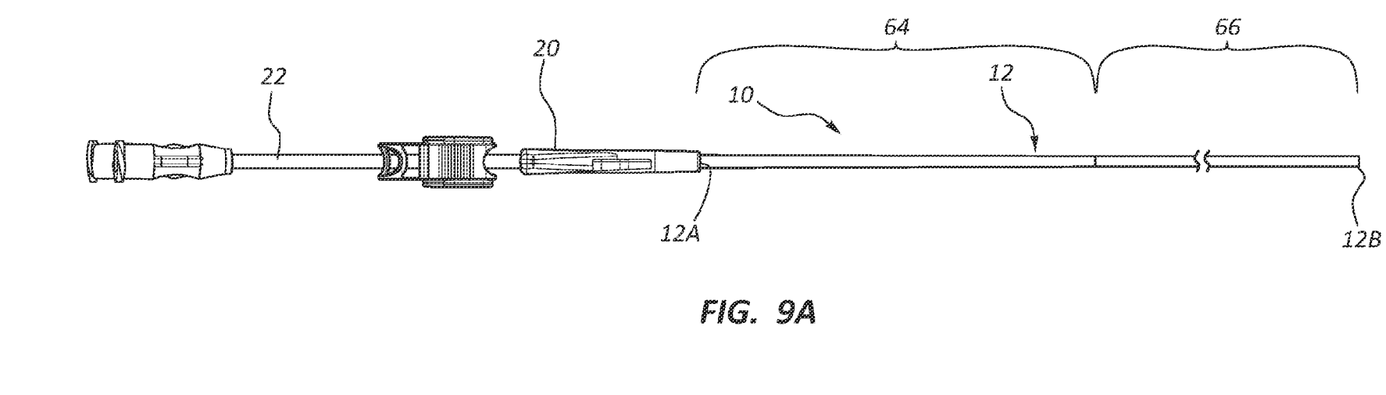
FIGS. 9A and 9B are side and top views, respectively, of a catheter assembly in accordance with one embodiment.
Figure 9B:
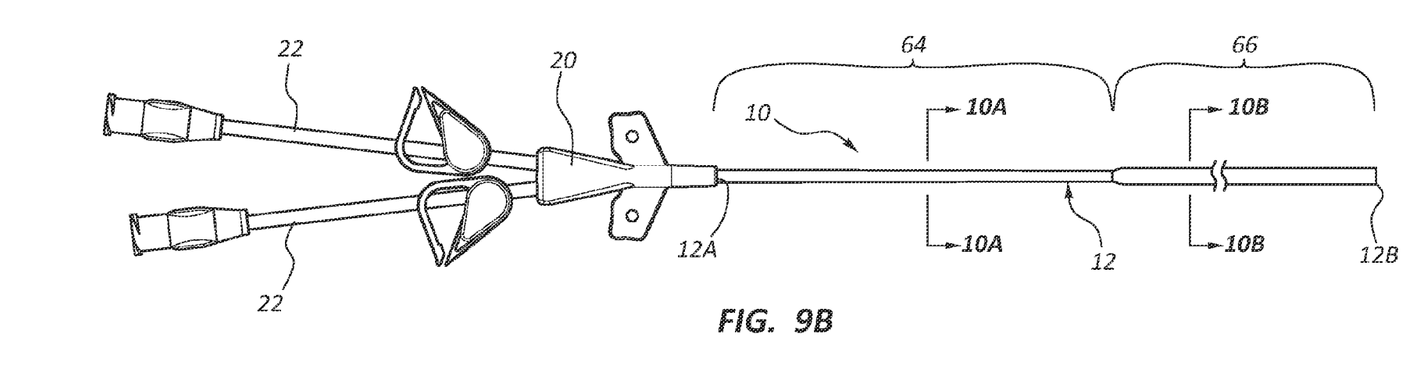
Figure 10A:
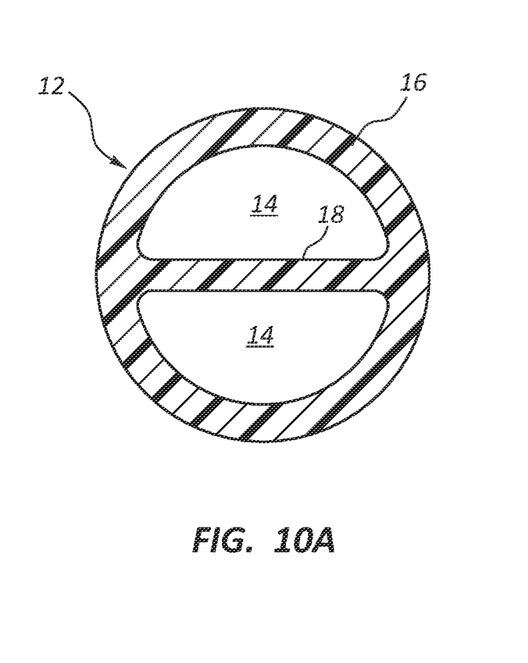
FIGS. 10A and 10B are cross sectional views of the catheter assembly of FIG. 9B.
Figure 10B:
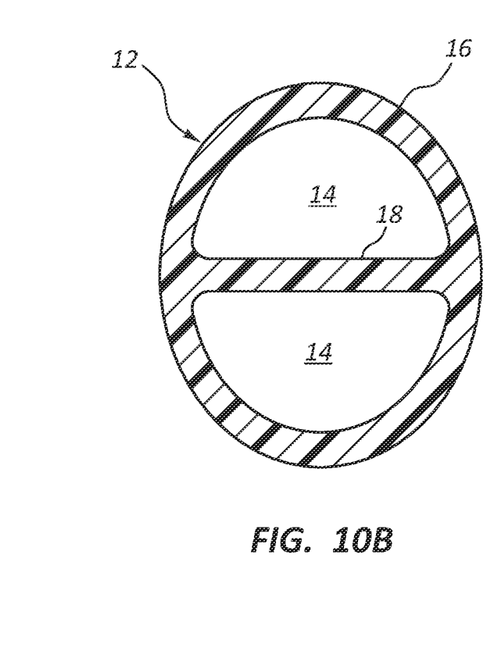

FIGS. 9A and 9B show side and top views, respectively, of the catheter assembly 10 according to one embodiment, wherein the dual lumen catheter tube 12 includes a proximal portion 64 extending distally from the bifurcation 20 and a distal portion 66 extending distally from the distal termination of the proximal portion to the distal tip of the catheter tube. In particular, the proximal portion 64 of the illustrated embodiment includes a circular cross-sectional profile, as seen by the sectional view of FIG. 10A. The distal portion 66 of the catheter tube includes an elliptical cross-sectional profile, similar to the configuration shown in FIG. 1B, as seen by the sectional view of FIG. 10B.

Observation of FIGS. 9A and 9B shows that the distal portion 66 increases in diameter with respect to the proximal portion 64, best seen in the top view of FIG. 9B, owing to the elliptical nature of the distal portion. In one embodiment, this provides desirably low hydraulic resistance in the distal portion of each lumen 14, as well as enhanced power injection behavior, e.g., relatively low power injection pressures and relatively greater distal tip stability. Moreover, the round proximal portion 64 of the catheter tube of FIGS. 9A and 9B is less likely to flip when the catheter tube is maneuvered within the vasculature during and after placement procedures.

As such, it is appreciated that a portion of the catheter tube may include an elliptical profile while other portions do not. In another embodiment it is appreciated that the positions of the circular and elliptical portions of the catheter tube can be reversed. In yet another embodiment, the average diameter of the proximal or distal portion of the catheter tube can increase relative the other. More generally, the size, number, length, lumen number, and placement of one or more elliptical portions of the catheter tube can vary as appreciated by one skilled in the art. Moreover, it is understood that the nature and/or degree/magnitude of the elliptical profile can vary over the length of the catheter tube. Further details regarding catheters that include features for enhancing the stability of a distal tip thereof can be found in U.S. application Ser. No. 13/209,270, filed Aug. 12, 2011, and entitled "Trimmable Catheter Including Distal Portion Stability Features," which is incorporated herein by reference in its entirety.

Figure 11A:
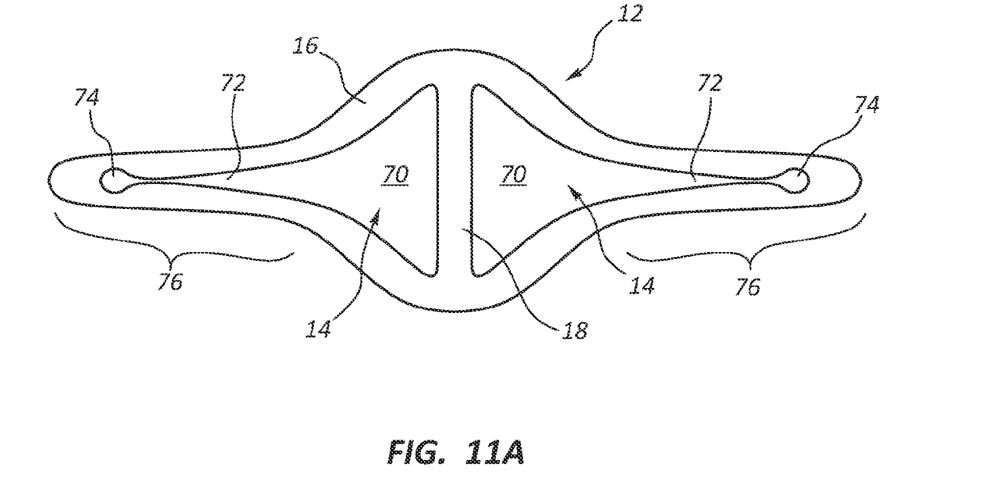
FIGS. 11A and 11B are cross sectional views of a catheter tube configured in accordance with one embodiment, both before and during fluid infusion, respectively.
Figure 11B:
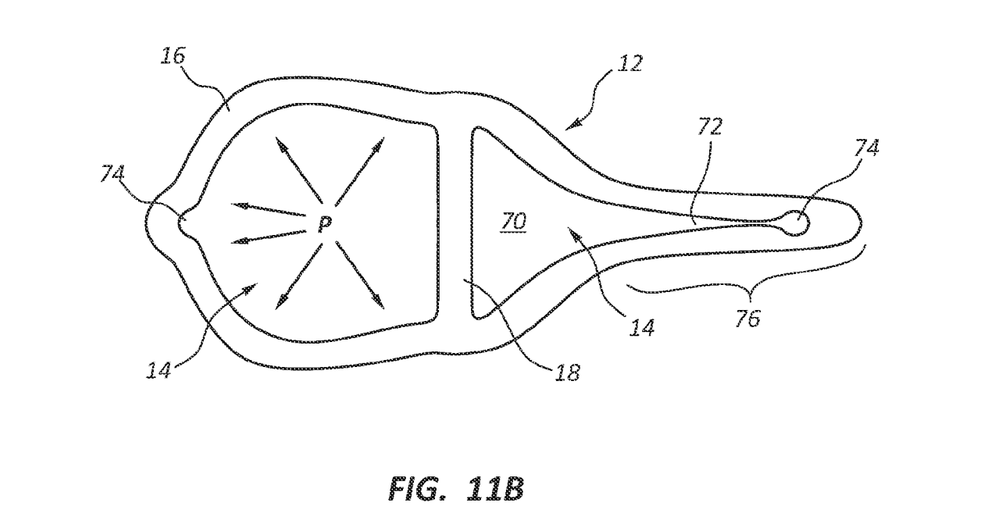

FIGS. 11A and 11B show a cross section of the catheter tube 12 according to another embodiment, wherein the two lumens 14 include an expandable profile. In particular, each lumen 14 includes an open, or patent, portion 70 proximate the septum 18 dividing the lumens and an initially collapsed portion 72 relatively farther away from the septum. At the folded, far end of each collapsed portion 72 an eyelet 74 is optionally included at a fold-point of the outer wall 16 to enhance expansion of the lumen 14 when fluid is passed therethrough. So configured, the collapsed portions 72 of the catheter tube lumens 14 define a pair of wings 76, thus giving the catheter tube 12 a "flying saucer"-like cross-sectional profile.

FIG. 11B shows the profile of the catheter 12 when one of the lumens 14 is pressurized with a pressure P, such as during power injection or other form of fluid infusion. As shown, the collapsed portion 72 expands such that the patent portion 70 and the collapsed portion combine and the overall lumen area increases. Note that the eyelet 74 enables the outer wall 16 to readily expand to accommodate the increased lumen size. When the pressure is removed, the lumen 14 returns to the original size shown in FIG. 11A. This process can be employed for either of the lumens 14, and can occur in both simultaneously. In this way, an initially low profile catheter tube (FIG. 11A) can transform in size (FIG. 11B) to accommodate relatively higher fluid flows.

Figure 12:
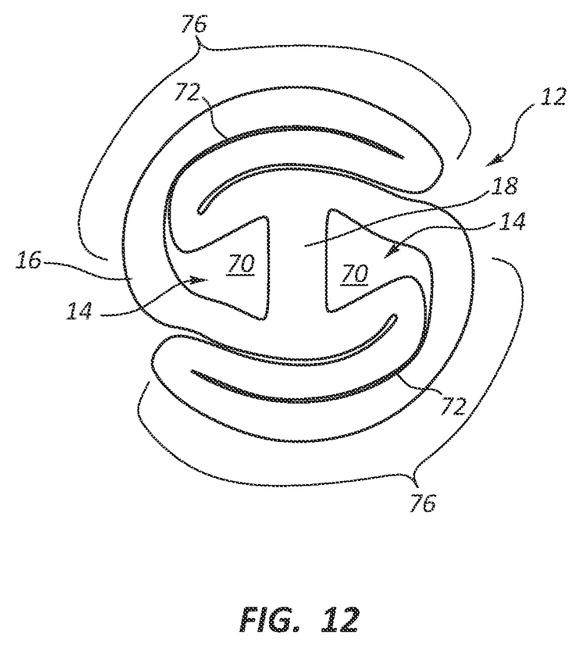
FIG. 12 is a cross-sectional view of the catheter tube of FIG. 11A in a rolled-up configuration.

FIG. 12 shows that, in one embodiment, a catheter tube, such as the catheter 12 of FIG. 11A, can be rolled in a rolled-up configuration so as to enable it to be placed in a round introducer, such as the introducer 60 shown in FIG. 8A. This enables the catheter tube to be inserted into a vessel or other body portion of the patient via use of the introducer. After insertion, the introducer can be removed from the vessel, which enables the catheter tube 12 to unroll and assume within the vessel the cross-sectional profile generally seen in FIG. 11A.

Figure 13:
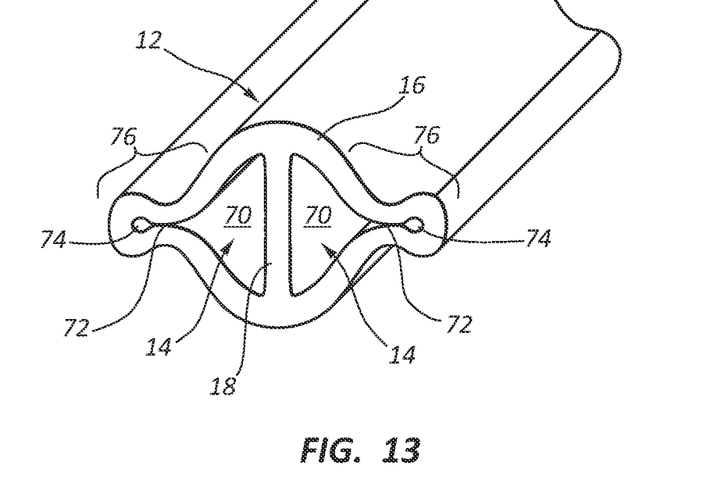
FIG. 13 is an end view of a catheter tube configured in accordance with one embodiment.
Figure 14:
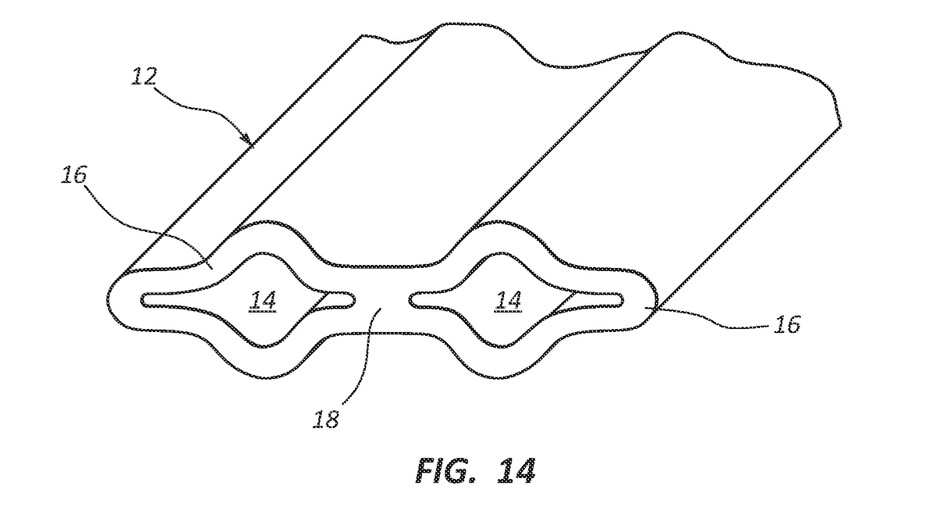
FIG. 14 is an end view of a catheter tube configured in accordance with one embodiment.

It is appreciated that the configuration of the winged catheter tube illustrated in FIGS. 11A-12 can vary in accordance with other embodiments. One example of this is shown in FIG. 13, wherein catheter tube 12 is more compact, resulting in the size of the collapsed portions 72 and corresponding length of the wings 76 being shorter relative those of the configuration shown in FIG. 11A. Yet another example is shown in FIG. 14, wherein the two lumens 14 are defined by the outer wall 16 and septum 18 so as to be positioned side-by-side, and each lumen generally defines a star-shaped or flying saucer-shaped cross-sectional profile. It should therefore be understood that these and other variations of the principles described herein are contemplated and that the cross-sectional profiles of the multi-lumen catheter tubes disclosed herein can vary as appreciated by one skilled in the art.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A catheter, comprising:
an elongate catheter tube defining a plurality of lumens, at least a portion of a longitudinal length of the catheter tube defining an elliptical cross section having a major axis and a minor axis, wherein a ratio of the major axis to the minor axis of the elliptical cross section is between about 1.3 and about 1.4, the plurality of lumens including a first lumen and a second lumen, each of the first and second lumens having corners that are rounded,
wherein a septum divides the first and second lumens, the septum defining a slackened configuration when the catheter is in an unstressed state to enable the catheter tube to assume a substantially circular cross section when inserted into a round introducer, the septum having a stiffness to prevent deflection when pressure differentials exist between the first and second lumens.

2. The catheter as defined in claim 1, wherein the first and second lumens arranged in a generally double-D configuration, wherein substantially an entire length of the catheter tube defines the elliptical cross section.

3. The catheter as defined in claim 1, wherein the septum changes from the slackened configuration to a taught configuration when the catheter tube is inserted into the round introducer.

4. The catheter as defined in claim 1, wherein the septum defines a wave-like shape in the slackened configuration.

5. The catheter as defined in claim 1, wherein the minor axis is substantially parallel with the septum.

6. The catheter as defined in claim 1, wherein the minor axis defines an angle with respect to the septum.

7. The catheter as defined in claim 1, wherein the plurality of lumens includes a third lumen, a portion of the septum being parallel to the minor axis.

8. The catheter as defined in claim 7, wherein the third lumen is power injectable and defines one of a round and a triangular cross sectional profile.

9. The catheter as defined in claim 8, wherein portions of the septum and an outer wall of the catheter tube that define the power injectable third lumen include a material having a durometer that is greater than a durometer of remaining portions of the septum and the outer wall of the catheter tube.

10. The catheter as defined in claim 1, wherein the plurality of lumens includes a third lumen, wherein at least two of the plurality of lumens are bisected by one of the minor axis and the major axis, at least one of the plurality of lumens being power injectable.

11. The catheter as defined in claim 1, wherein a proximal portion of the catheter tube defines a circular cross section and wherein a distal portion of the catheter tube defines the elliptical cross section.

12. The catheter as defined in claim 11, wherein an average outer diameter of the distal portion of the catheter tube is greater than an average outer diameter of the proximal portion of the catheter tube so as to enhance stability of a distal tip of the catheter tube during fluid infusion when the catheter tube is disposed within a vessel of a patient.

13. The catheter as defined in claim 1, wherein a proximal portion of the catheter tube defines the elliptical cross section and wherein a distal portion of the catheter tube defines a circular cross section.

14. The catheter as defined in claim 1, wherein a wall thickness of the catheter tube equals about 20% of an average outer diameter of the catheter tube, defined as the sum of an outer diameter at the major axis and an outer diameter at the minor axis divided by 2.

15. A catheter, comprising:
an elongate catheter tube defining a plurality of lumens, wherein:
at least a portion of a longitudinal length of the catheter tube defines an elliptical cross section having a major axis and a minor axis;
a ratio of the major axis to the minor axis of the elliptical cross section is between about 1.3 and about 1.4;
the plurality of lumens includes a first lumen, a second lumen, and a third lumen;
each of the first and second lumens have corners that are rounded;
at least two of the plurality of lumens are bisected by one of the major axis and the minor axis; and
at least one of the plurality of lumens is power injectable.

16. The catheter as defined in claim 15, wherein the longitudinal length of the catheter tube defines the elliptical cross section.

17. The catheter as defined in claim 15, wherein a septum divides the first and second lumens, the septum defining a slackened configuration when the catheter is in an unstressed state to enable the catheter tube to assume a substantially circular cross section when inserted into a round introducer, the septum having a stiffness to prevent deflection when pressure differentials exist between the first and second lumens.

18. The catheter as defined in claim 17, wherein the septum changes from a slackened configuration to a taught configuration when the catheter tube is inserted into the round introducer.

19. The catheter as defined in claim 17, wherein the septum defines a wave-like shape in the slackened configuration.

20. The catheter as defined in claim 15, wherein the first and second lumens are separated by a septum, the minor axis being substantially parallel with the septum.

21. The catheter as defined in claim 15, wherein the first and second lumens are separated by a septum, the minor axis defining an angle with respect to the septum.

22. The catheter as defined in claim 15, wherein the plurality of lumens are separated by at least one septum, at least a portion of the septum being parallel to the minor axis.

23. The catheter as defined in claim 15, wherein the third lumen is power injectable and defines one of a round and a triangular cross sectional profile.

24. The catheter as defined in claim 23, wherein portions of the septum and an outer wall of the catheter tube that define the power injectable third lumen include a material having a durometer that is greater than a durometer of remaining portions of the septum and the outer wall of the catheter tube.

25. The catheter as defined in claim 15, wherein a proximal portion of the catheter tube defines a circular cross section and wherein a distal portion of the catheter tube defines the elliptical cross section.

26. The catheter as defined in claim 25, wherein an average outer diameter of the distal portion of the catheter tube is greater than an average outer diameter of the proximal portion of the catheter tube so as to enhance stability of a distal tip of the catheter tube during fluid infusion when the catheter tube is disposed within a vessel of a patient.

27. The catheter as defined in claim 15, wherein a proximal portion of the catheter tube defines the elliptical cross section and wherein a distal portion of the catheter tube defines a circular cross section.

28. The catheter as defined in claim 15, wherein a wall thickness of the catheter tube equals about 20% of an average outer diameter of the catheter tube, defined as a sum of an outer diameter at the major axis and an outer diameter at the minor axis divided by 2.

* * * * *